US009814358B2

(12) United States Patent
Brunelle

(10) Patent No.: US 9,814,358 B2
(45) Date of Patent: Nov. 14, 2017

(54) AROMATIC MISTING SYSTEM AND METHOD FOR USE WITH A BATHTUB

(71) Applicant: GESTION ULTRA INTERNATIONALE INC., St-Nicolas (CA)

(72) Inventor: Henry Brunelle, Quebec (CA)

(73) Assignee: GESTION ULTRA INTERNATIONALE INC., St-Nicolas (CA)

( * ) Notice: Subject to any disclaimer, the term of this patent is extended or adjusted under 35 U.S.C. 154(b) by 192 days.

(21) Appl. No.: 14/719,371

(22) Filed: May 22, 2015

(65) Prior Publication Data

US 2015/0335205 A1    Nov. 26, 2015

(30) Foreign Application Priority Data

May 26, 2014   (CA) ..................................... 2852596

(51) Int. Cl.
| | | |
|---|---|---|
| *A47K 3/00* | (2006.01) | |
| *B01F 3/04* | (2006.01) | |
| *A61H 33/00* | (2006.01) | |
| *A61L 9/14* | (2006.01) | |
| *A47K 3/10* | (2006.01) | |

(52) U.S. Cl.
CPC .............. *A47K 3/001* (2013.01); *A61H 33/60* (2013.01); *A61L 9/14* (2013.01); *B01F 3/04014* (2013.01); *B01F 3/04021* (2013.01); *A47K 3/10* (2013.01); *A61H 2201/102* (2013.01); *A61L 2209/132* (2013.01); *B01F 2215/009* (2013.01)

(58) Field of Classification Search
CPC ..... A61H 33/60; A47K 3/001; B01F 3/04014; B01F 3/04021; B05B 17/06; B05B 17/0615; B05B 17/0653
USPC .................... 4/546, 661; 239/4, 322; 261/30
See application file for complete search history.

(56) References Cited

U.S. PATENT DOCUMENTS

| | | |
|---|---|---|
| 3,901,443 A | 8/1975 | Mitsui et al. |
| 4,410,139 A | 10/1983 | Nishikawa et al. |
| (Continued) | | |

OTHER PUBLICATIONS

Hamlin, Position and Movement Sensor Solutions. Technical Information : Reed Switch. http://www.hamlin.com/technical-detail-reed-switch.cfm. Retrieved from Internet on Sep. 8, 2012.

*Primary Examiner* — Viet Le
(74) *Attorney, Agent, or Firm* — Norton Rose Fulbright Canada LLP; Alexandre Daoust

(57) ABSTRACT

An aromatic misting system for use with a bathtub comprises a reservoir having an open top end in which a removable cover structure is disposed. The cover structure has an orifice through which an aromatic mist is discharged. A liquid atomizing piezoelectric element is sealingly secured at a bottom end of the reservoir. The cover structure has a switch actuator when disposed at one position. When the cover is positioned at a second closed position, the reservoir is closed and the switch is not actuated. When there is hot water in the bathtub, the aromatic mist created in the reservoir is drawn out by the hot air generated by hot water placed in the bathtub adjacent the cover orifice, thus creating a temperature differential between the hot air and the cooler mist generated in the reservoir wherein the mist is drawn out by the temperature differential and propagates into a misty cloud over the bathtub.

15 Claims, 5 Drawing Sheets

(56) References Cited

U.S. PATENT DOCUMENTS

| | | | |
|---|---|---|---|
| 4,601,886 A | 7/1986 | Hudgins | |
| 4,603,030 A | 7/1986 | McCarthy | |
| 5,023,020 A | 6/1991 | Machida et al. | |
| 5,217,165 A | 6/1993 | Takahashi et al. | |
| 5,881,714 A | 3/1999 | Yokoi et al. | |
| 6,619,559 B2 | 9/2003 | Wohrle | |
| 7,350,721 B2 | 4/2008 | Ghazarian | |
| 7,687,744 B2 | 3/2010 | Walter et al. | |
| 7,934,703 B2 * | 5/2011 | Tomono | A01M 1/205 261/127 |
| 7,963,460 B2 | 6/2011 | Jörgensen | |
| 7,992,801 B2 | 8/2011 | Jörgensen | |
| 8,070,669 B2 | 12/2011 | Brunelle et al. | |
| 8,137,630 B2 | 3/2012 | Jörgensen | |
| 8,196,903 B2 | 6/2012 | Jörgensen | |
| 2005/0217016 A1 * | 10/2005 | Ciechanowski | A61K 8/02 4/559 |
| 2012/0036626 A1 * | 2/2012 | Vogtner | A61H 33/60 4/541.1 |

* cited by examiner

AROMATIC MISTING SYSTEM AND METHOD FOR USE WITH A BATHTUB

TECHNICAL FIELD

This specification relates to an aromatic misting system for use with a bathtub.

BACKGROUND ART

It is known that some aroma have substantial physiological effects on people. For example, some aroma having a lemon scent has a stimulant effect or act as cures for drowsiness because they excite people mentally and they activate the circulatory system. Also, aroma diffused by lavender have effects of relieving stress, anxiety or the like and further have anti-depressive effects because they relax tension. Aroma diffused with rosemary and the like plants have orexigenic and relaxative effects. Other compounds are also known that when admixed with water and diffused in a mix have effects of sterilization against harmful bacteria or virus and therefore have effects of restoration of good health to people.

Nebulizers or diffusers are usually utilized to dispense aromas and essential oils in a mist in an environment. These scented mists are in contact with the wall of the diffuser chamber which tends to be contaminated with aromatic fluid stains or essential oil stains. This requires periodic cleaning of the device and the dismantling of those parts in contact with the scented oil mist and this is often problematic and time-consuming.

In these atomizing devices, the mist is usually released in the environment by a fan associated with the device. These fans generate noise and interfere with the relaxing effects of the aromatic mist and the environment in which a person is disposed for relaxation. These devices also consist of many parts and are therefore costly and prone to malfunction.

SUMMARY OF INVENTION

In accordance with one aspect, there is provided an aromatic misting system for use with a bathtub having a top opening, said misting system comprising a reservoir having an open top end, a removable cover structure disposed in said open top end, directional orifice means in said cover structure, liquid atomizing means sealingly secured at a bottom end of said reservoir for producing a mist from an aromatic liquid disposed in said reservoir, said cover structure having switch actuation means for actuating a switch to enable said liquid atomizing means when said cover structure is positioned into said open top end, level sensing means to sense the level of said liquid in said reservoir, and air stream convection means to draw said mist from said directional orifice of said reservoir and into the top opening of said bathtub where a user person positions itself.

According to another broad aspect, the present invention provides a method of providing an aromatic mist in a bathtub comprising the steps of:

i) securing a reservoir as claimed in claim 1 on a ledge of said bathtub and adjacent said top opening thereof;

ii) filling said reservoir with water in admixture with an aromatic substance and/or essential oils;

iii) fitting said cover structure in said open top end of said reservoir and at a predetermined position on said ledge of said bathtub; and iv) actuating said liquid atomizing means to produce said mist, and wherein said mist containing an aromatic scent and/or essential oils will flow out of said reservoir and into said top opening to form a cloudy mist.

BRIEF DESCRIPTION OF DRAWINGS

A preferred embodiment of the present invention will now be described with reference to the accompanying drawings in which.

DESCRIPTION OF PREFERRED EMBODIMENTS

Figure 1:
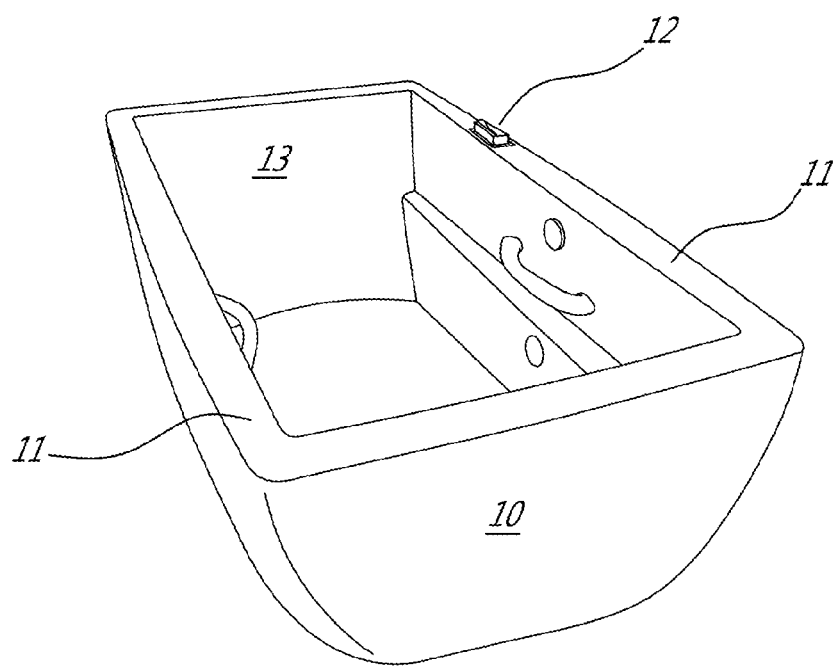
FIG. 1 is a top perspective view of the bathtub on the ledge of which is incorporated the aromatic misting system of the present invention.

Referring now to the drawings and more particularly to FIG. 1, there is shown generally at 10 a bathing tub having a contour ledge 11 in which is secured the aromatic mist producing device 12 of the present invention in combination with a bathtub. The bathtub may also be a hydro massage tub, etc. The mist producing device 12 is located adjacent an end 13 of the bathtub where a user person is usually sitting to receive a relaxing treatment by the mist. The mist producing device is disposed at any location on the ledge portion of the bathtub whereby the user person will benefit from the essential oils and aromas present in a mist produced in the device 12. It is preferred that the bathtub be filled with hot water to enhance the relaxing benefit, but the mist producing device operates without hot air present at its outlet.

Figure 7:
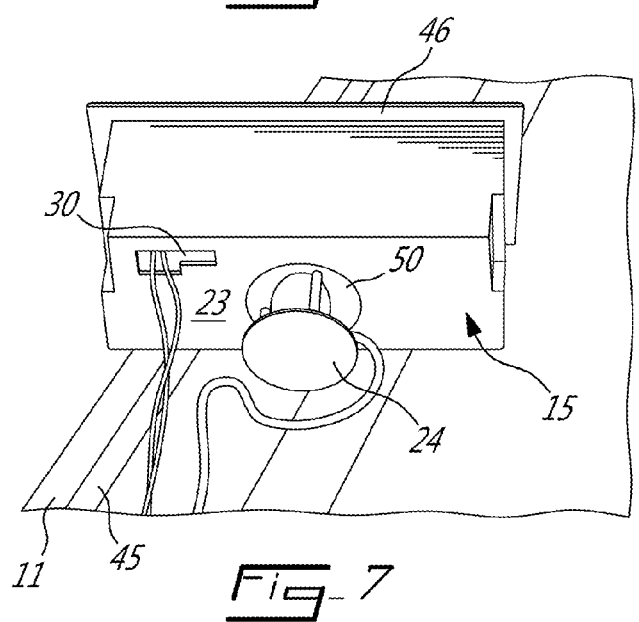
FIG. 7 is a bottom view of the reservoir showing the position of the reed switch and the piezoelectric transducer.
Figure 8:
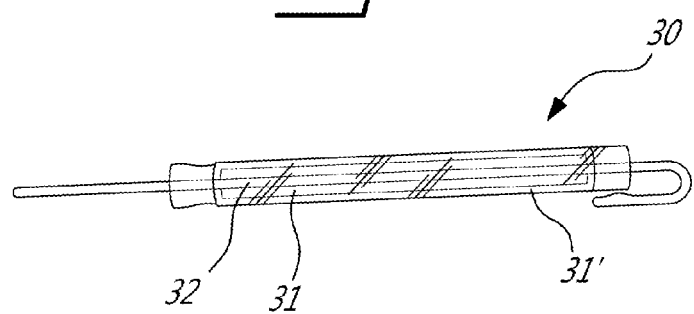
FIG. 8 is a perspective view of a reed switch.
Figure 9:
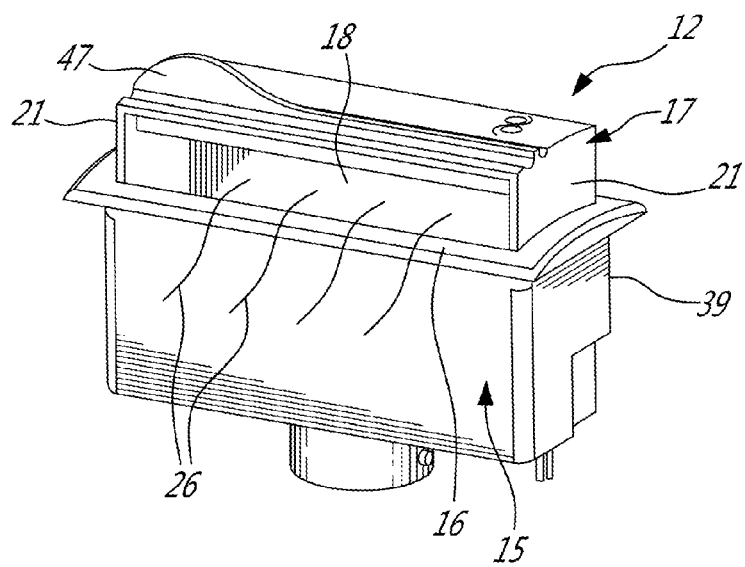
FIG. 9 is a perspective view showing the construction of the reservoir.
Figure 10:
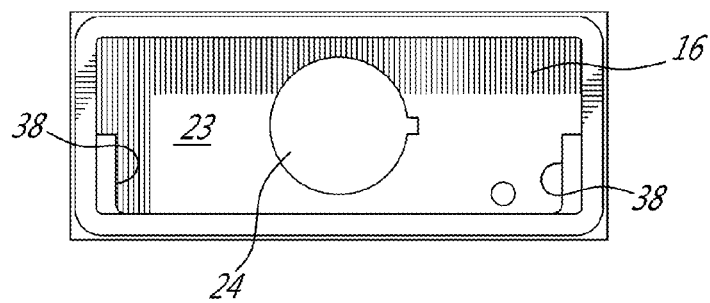
FIG. 10 is a top view of the reservoir with the cover removed.
Figures 11A, 11B:
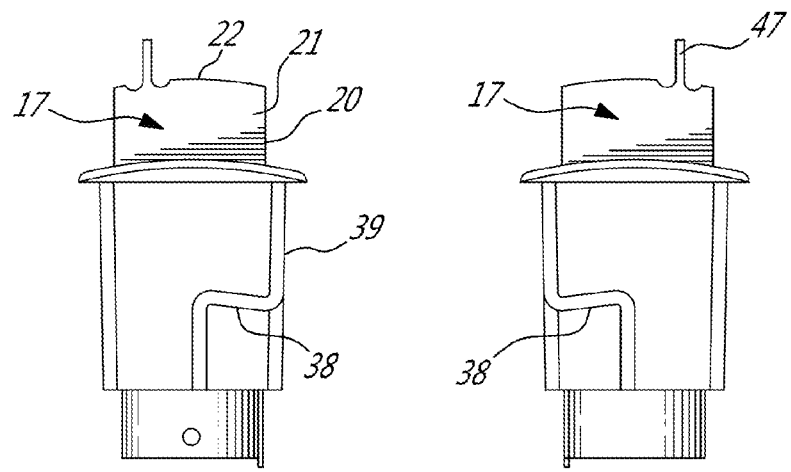
FIGS. 11A and 11B are sectional side views of the reservoir.
Figure 12:
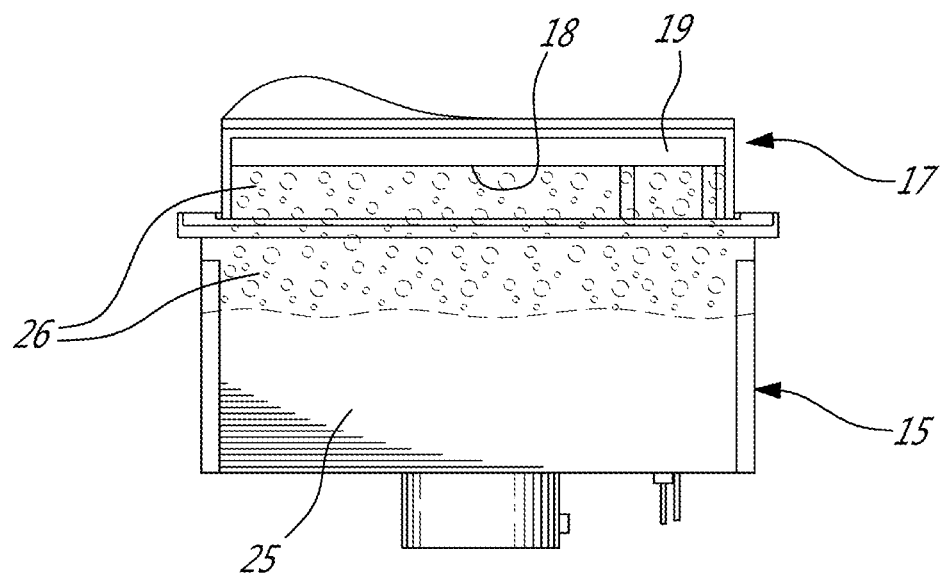
FIG. 12 is a sectional front view of the reservoir.
Figure 13:
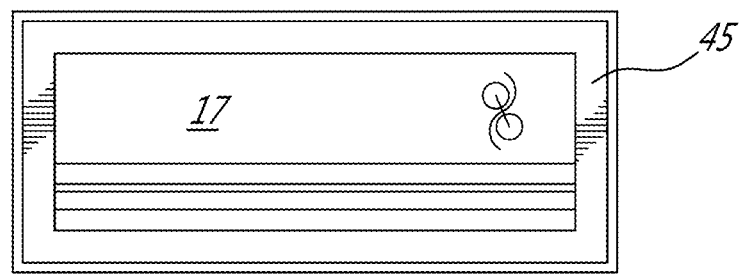
FIG. 13 is a top view of FIG. 9.

FIGS. 9 to 13 show the construction of the mist producing device 12. As hereinshown, the device comprises a reservoir 15 which has an open top end 16. A removable cover structure 17 is removably disposed in the open top end 16. The cover has a directional orifice 18 formed in a side wall 19 thereof. The cover has a closed rear wall 20 and opposed side walls 21 and a top wall 22. The construction of the removable cover 17 is also well illustrated in FIG. 2. The reservoir 15 has a bottom wall 23 in which is secured a piezoelectric diffusing element 24 which vibrates at high frequency whereby to atomize the liquid 25 (see FIG. 12) placed in the reservoir to produce a mist. The liquid 25 is admixed with essential oils or aromatic substances or a combination whereby an aromatic mist, as illustrated by flow lines 26 in FIG. 9, is caused to exit the directional orifice 18 in a manner as will be described later. As shown in FIG. 7, the bottom wall 23 is also provided with a switch, herein a reed switch 30, secured thereto at a predetermined location. The reed switch 30 is better illustrated in FIG. 8 and is of a conventional design. The basic reed switch consists of two ferromagnetic nickel-iron wires 31 located in a glass capsule 32. The two wires 31 and 31' have a flat free end inside the glass capsule 32 which are spaced-apart to form a gap. These two reeds act as magnetic flux conductors and when exposed to an external magnetic field from a permanent magnet the contacts will close. Accordingly, the reed switch is a normally open contact switch (biased to the open condition by default).

Figure 6:
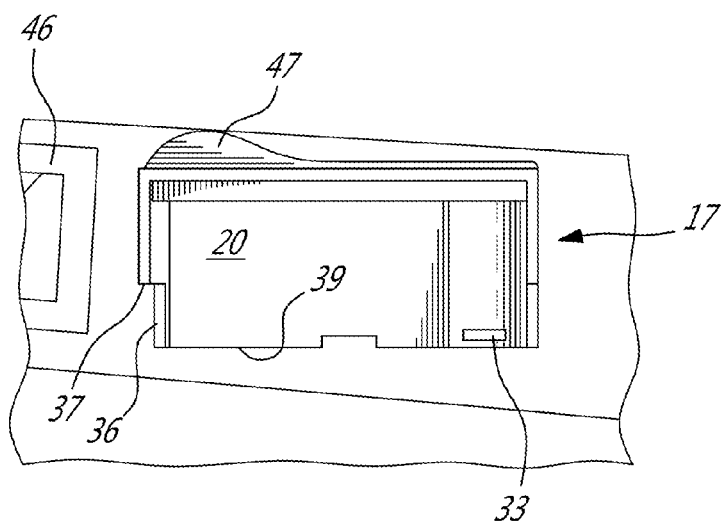
FIG. 6 is a top view of the cover showing the lower ledge construction thereof and the location of the magnetic element.

As shown in FIG. 6, the rear wall 20 of the removable cover 17 is provided with a permanent magnet 33 embedded or otherwise secured adjacent a lower edge 34 of the rear wall 20 and disposed at a location such that when the cover is in a first operative position, as shown in FIG. 9, the permanent magnet 33 is disposed close to the reed switch causing the switch to close and operate the piezoelectric transducer if there is liquid in the reservoir. Accordingly, the cover acts as a switch actuator.

Figure 4:
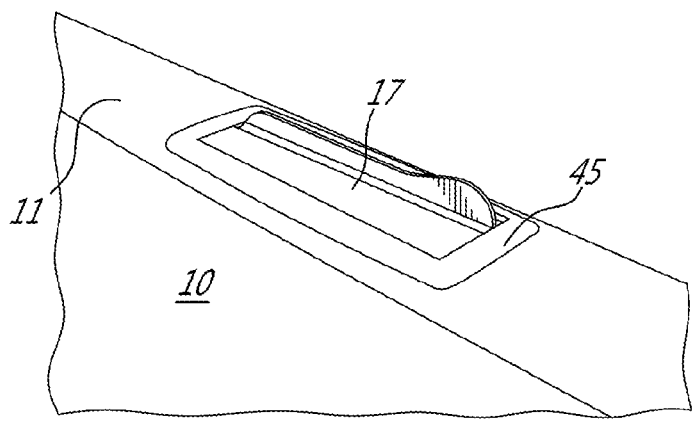
FIG. 4 is a perspective view, similar to FIG. 3, showing the cover in a closed position.
Figure 5:
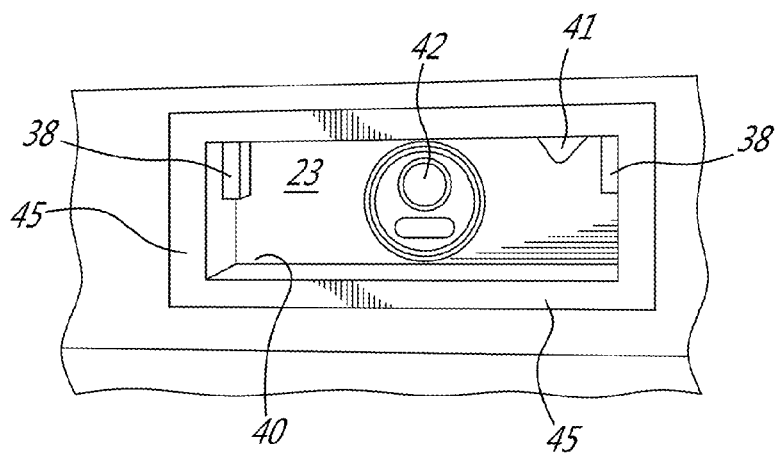
FIG. 5 is a top view illustrating the inner construction of the reservoir showing the position of the piezoelectric transducer, level sensor and cover support as well as the reed switch position.

As also shown in FIG. 6, the cover end walls 21 also have an undercut portion 36 thus defining a seating formation 37 for seating engagement on support formations 38 (see FIGS. 10, 11A and 11B) formed in the reservoir for supporting the cover structure at a first open operative position as shown in FIG. 9. When the cover is disposed in a closed position, as shown in FIG. 4, by rotating the cover with the orifice 18 facing the rear wall 39 of the housing, the seating formation 37 or ledge no longer rests on the support formations 38 and accordingly, the lower edge 39 of the rear wall 20 of the cover will sit on the bottom wall 23 of the reservoir. Further, the permanent magnet 33 is now located away from the reed switch in an opposed corner 40 (see FIG. 5) of the reservoir and the switch will not close. In FIG. 5, the reed switch is shown located in a depression formed in the wall of the reservoir, namely in the protrusion 41, as seen from inside the reservoir. The piezoelectric transducer assembly is also provided with a level sensor 42 at a proper location therein, which projects into the housing to sense the level of liquid in the reservoir. The sensor cuts out the piezoelectric element when the water level is too low to produce a mist from the remaining liquid in the reservoir.

Figure 2:
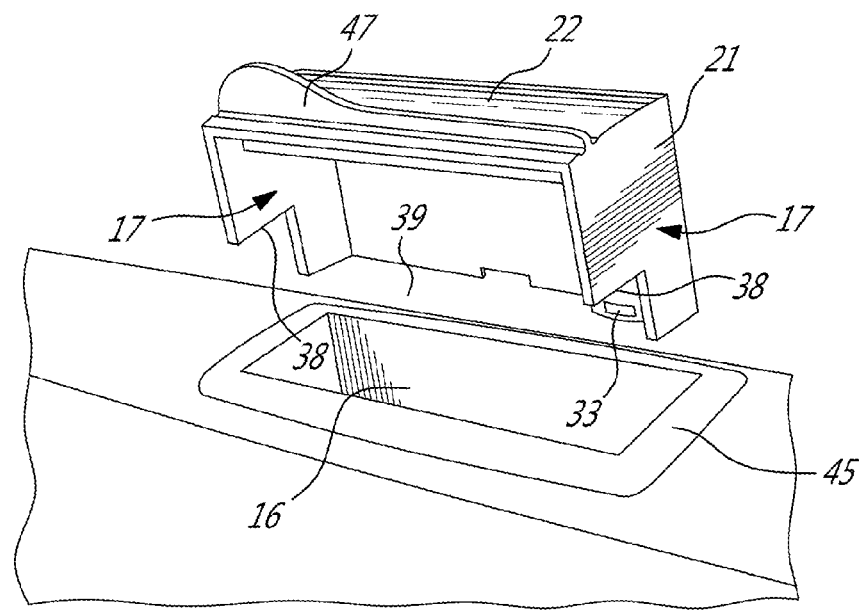
FIG. 2 is a perspective view illustrating the construction of the cover showing the cover being removed from the reservoir.
Figure 3:
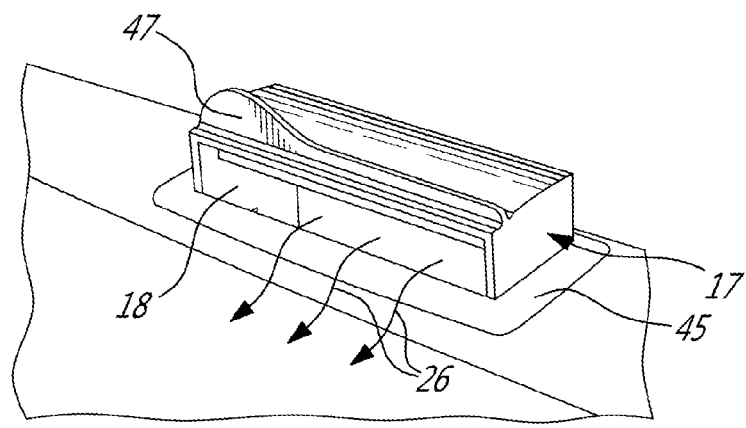
FIG. 3 is a perspective view showing the cover disposed in a first position wherein the directional orifice is open.

Referring to FIGS. 6 and 7, it can be seen that in order to mount the misting system or device 12, a cavity 45 is formed in the ledge 11 of the bathtub. The reservoir 15 is also provided with a top contour flange 46 and a double-sided adhesive tape is disposed behind and about the flange to attach the reservoir in a seal-type manner around the cavity to prevent the infiltration of water. As shown in FIG. 6, the cover is also provided with a gripping top flange 47 to facilitate the removal and insertion of the removable cover 17 into the top open end of the reservoir, as is illustrated in FIG. 2.

In operation, the reservoir is filled with water and essential oils and/or other aromatic liquid substances. The bathtub is also filled with warm water to a predetermined level or the bathtub may remain empty to act as an open enclosure. The cover of the reservoir is pushed into the reservoir whereby to actuate the reed switch which enables the piezoelectric transducer module. The cover is disposed such that the directional orifice 18 faces inwardly of the bathtub. A hot air mist is produced in the reservoir above the water level by the hot water in the bathtub and is present at the directional orifice 18. The hot air above the water level of the bathtub creates a hot environment adjacent the directional orifice 18 wherein the cool mist generated by the piezoelectric transducer creates a temperature differential at the orifice 18 between the hot air of the bathtub and the cold air of the mist, drawing the mist out of the reservoir through this directional orifice to mix with hot vapors present on the surface of the bathtub. This also creates a misty cloud over the bathtub in the presence of the user person and close to the face of the user person where aromatic vapors are deposited on the exposed body portions of the user wherein essential oil droplets will deposit and provide a smoothness to the skin and a soothing treatment and facial treatment depending on the essential oils admixed with the water in the reservoir. The reservoir can be positioned at any location along the contour ledge of the bathtub. Also, as mentioned above, the bathtub may not have water therein and only acts as an open enclosure to support a user person. The mist created by the piezoelectric transducer would simply be forced out of the housing by the volume produced in the enclosure and propagate in the area of the bathtub and slowly descend in the bathtub.

The cleaning of the misting system is simplified in that the cover is removable and can be cleaned separately from the reservoir. Because the reservoir is completely open, it facilitates the insertion of a sponge pad or cloth as well as cleaning liquids or sprays inside the reservoir for cleaning. The reservoir is hereinshown constructed of ABS plastics and the piezoelectric transducer is tightly secured to the bottom wall on a gasket 50, as shown in FIG. 7. As also shown in that Figure, the piezoelectric transducer 24 is not exposed to the water within the reservoir. The piezoelectric transducer has a dome-shaped sealed casing through which high frequencies are generated into the liquid. Accordingly, the inner surface of the reservoir is a sealed surface.

It is within the ambit of the present invention to cover any obvious modifications of the preferred embodiment described herein, provided such modifications fall within the scope of the appended claims.

The invention claimed is:

1. An aromatic misting system for use with a bathtub having a top opening, said misting system comprising a reservoir having an open top end, a removable cover structure disposed in said open top end, directional orifice means in said cover structure, liquid atomizing means sealingly secured at a bottom end of said reservoir for producing a mist from an aromatic liquid disposed in said reservoir, said removable cover structure having switch actuation means for actuating a switch to enable said liquid atomizing means when said removable cover structure is positioned into said open top end, level sensing means to sense the level of said liquid in said reservoir, and air stream convection means to draw said mist from said directional orifice of said reservoir and into the top opening of said bathtub where a user person positions itself.

2. An aromatic misting system as claimed in claim 1 wherein said bathtub when said bathtub is filled to a predetermined level with hot water wherein the differential temperature between hot air at said directional orifice created by said hot water will cause said mist which is at a cooler temperature to be drawn out of said reservoir through said directional orifice to mix with said hot air at said predetermined area.

3. An aromatic misting system as claimed in claim 1 wherein said removable cover structure is positionable in said open top end at a first and second position, said first position permitting said switch actuation means to actuate said switch, said second position concealing said directional orifice means and preventing actuation of said switch.

4. An aromatic misting system as claimed in claim 1 wherein said liquid atomizing means is a piezo-electric transducer module provided with said level sensing means sealingly mounted on a bottom wall of said reservoir.

5. An aromatic misting system as claimed in claim 1 wherein said switch actuation means is a switch actuating formation formed in a depending wall of said removable cover structure for actuating said switch.

6. An aromatic misting system as claimed in claim 5 wherein said switch is a reed switch secured under a lower portion of said reservoir, said switch actuating formation being a magnetic element secured at a predetermined location in a lower portion of said depending wall for positioning relative to said reed switch to cause a contact closure of said reed switch.

7. An aromatic misting system as claimed in claim 1 wherein said reservoir has a top contour flange for securement of said reservoir in an opening formed in an upper ledge of said bathtub adjacent said top opening where said user person positions itself.

8. An aromatic misting system as claimed in claim 1 wherein said liquid is water in admixture with an aromatic substance and/or essential oils to produce an aromatic mist in said reservoir.

9. An aromatic misting system as claimed in claim 3 wherein said removable cover structure has at least one depending wall having a seating formation at a lower end thereof for seating engagement on a support formation formed in said reservoir for supporting said removable cover structure at said first position, said removable cover structure when at said second position disposing said seating formation away from said support formation.

10. A method of providing an aromatic mist in a bathtub comprising the steps of:
   i) securing a reservoir as claimed in claim 1 on a ledge of said bathtub and adjacent said top opening thereof;
   ii) filling said reservoir with water in admixture with an aromatic substance and/or essential oils;
   iii) fitting said removable cover structure in said open top end of said reservoir and at a predetermined position on said ledge of said bathtub; and
   iv) actuating said liquid atomizing means to produce said mist, and wherein said mist containing an aromatic scent and/or essential oils will flow out of said reservoir and into said top opening to form a cloudy mist.

11. A method as claimed in claim 10 wherein there is further provided the step of filling said bathtub with hot water, said mist being assisted in flowing out of said reservoir by the differential temperature by hot air at said directional orifice which will cause said mist which is at a cooler temperature to be drawn out of said reservoir through said directional orifice.

12. An aromatic misting system for use with a bathtub having a top opening, said misting system comprising a reservoir having an open top end, a removable cover structure disposed in said open top end, directional orifice means in said cover structure, and liquid atomizing means sealingly secured at a bottom end of said reservoir for producing a mist from an aromatic liquid disposed in said reservoir, said removable cover structure having switch actuation means for actuating a switch to enable said liquid atomizing means when said removable cover structure is positioned into said open top end, said removable cover structure being positionable in said open top end at a first and second position, said first position permitting said switch actuation means to actuate said switch, second position preventing actuation of said switch.

13. An aromatic misting system as claimed in claim 12 wherein said second position conceals said directional orifice means.

14. An aromatic misting system as claimed in claim 12 wherein said removable cover structure has at least one depending wall having a seating formation at a lower end thereof for seating engagement on a support formation formed in said reservoir for supporting said removable cover structure at said first position, said removable cover structure when at said second position disposing said seating formation away from said support formation.

15. An aromatic misting system for use with a bathtub having a top opening, said misting system comprising a reservoir having an open top end, a removable cover structure disposed in said open top end, directional orifice means in said cover structure, and liquid atomizing means sealingly secured at a bottom end of said reservoir for producing a mist from an aromatic liquid disposed in said reservoir, said removable cover structure having switch actuation means for actuating a switch to enable said liquid atomizing means when said removable cover structure is positioned into said open top end, wherein said switch actuation means is a switch actuating formation formed in a depending wall of said removable cover structure for actuating said switch, said switch being a reed switch secured under a lower portion of said reservoir, said switch actuating formation being a magnetic element secured at a predetermined location in a lower portion of said depending wall for positioning relative to said reed switch to cause a contact closure of said reed switch.

* * * * *